United States Patent [19]

Patchett et al.

[11] 4,351,844

[45] Sep. 28, 1982

[54] HYPOCHOLESTEROLEMIC HYDROGENATION PRODUCTS AND PROCESS OF PREPARATION

[75] Inventors: Arthur A. Patchett, Westfield; Chan-Hwa Kuo, South Plainfield, both of N.J.

[73] Assignee: Merck & Co., Inc., Rahway, N.J.

[21] Appl. No.: 210,826

[22] Filed: Dec. 1, 1980

Related U.S. Application Data

[63] Continuation-in-part of Ser. No. 118,050, Feb. 4, 1980, abandoned.

[51] Int. Cl.$^3$ .............. A61K 31/335; A61K 31/215; C07C 69/74; C07C 59/11
[52] U.S. Cl. .................................................. 424/279
[58] Field of Search ............... 260/343.5; 560/119, 560/256, 185; 562/501; 424/279, 305

[56] References Cited

U.S. PATENT DOCUMENTS

| 3,072,709 | 1/1963 | Saucy et al. | 560/107 |
|---|---|---|---|
| 3,344,169 | 9/1967 | Los | 560/107 |
| 4,231,938 | 11/1980 | Monaghan et al. | 260/343.5 |
| 4,282,155 | 8/1981 | Smith et al. | 260/343.5 |
| 4,293,446 | 10/1981 | Willard | 424/279 |
| 4,294,846 | 10/1981 | Albers-Schonberg et al. | 424/279 |
| 4,319,039 | 3/1982 | Albers-Schonberg et al. | 560/256 |
| 4,323,648 | 4/1982 | Tanzawa et al. | 260/343.5 |

Primary Examiner—Ethel G. Love
Attorney, Agent, or Firm—William H. Nicholson; Mario A. Monaco

[57] ABSTRACT

Hydrogenation of the natural fermentation product, mevinolin, MK-803, results in the production of dihydro- and tetra-hydro derivatives and hydrogenation of the naturally occurring dihydromevinolin results in the formation of a tetrahydro derivative. These several products with the exception of cis-(4α$\beta$, 8α$\beta$-)-tetrahydromevinolin are potent inhibitors of cholesterol biosynthesis.

10 Claims, No Drawings

HYPOCHOLESTEROLEMIC HYDROGENATION PRODUCTS AND PROCESS OF PREPARATION

This application is a continuation-in-part of copending application, Ser. No. 118,050, filed Feb. 4, 1980, now abandoned.

SUMMARY OF THE INVENTION

This invention relates to hypocholesterolemic products produced by hydrogenation of a compound of formula I and a naturally occurring dihydro analog thereof.

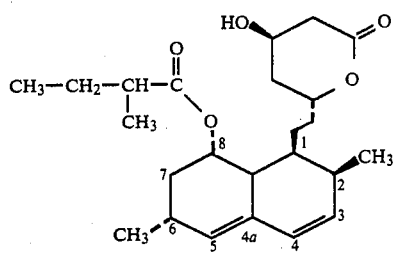

More specifically, it relates to compounds of the formula II and to the corresponding free hydroxy acid of formula III and to processes for their preparation.

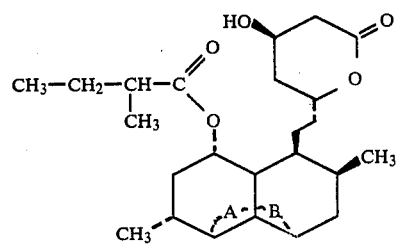

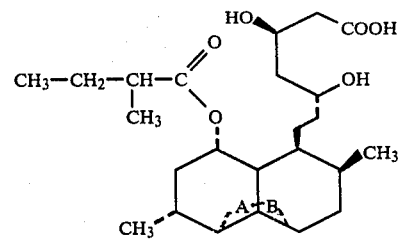

The dotted lines A and B represent optional double bonds not more than one of A and B being a double bond, as well as pharmaceutically acceptable salts of the latter and lower alkyl and substituted alkyl esters of the latter in which the possible substituent is phenyl, dimethylamino or acetylamino. These new compounds have excellent properties of inhibiting cholesterol biosynthesis and are useful against hypercholesterolemia and hyperlipemia.

BACKGROUND OF THE INVENTION

Because of the possible connection between high blood cholesterol and atherosclerosis, many efforts have been made to find ways and substances which would reduce the cholesterol in the mammalian body. One of these ways is to inhibit in mammals the body's ability to synthesize cholesterol.

Recently, Endo et al., described (U.S. Pat. Nos. 4,049,495 and 3,983,140) a fermentation product obtained by cultivation of a microorganism of the genus Penicillium and isolation from the medium. They called it ML236B and determined its structure together with two related compounds 236A and 236C. Its structure, under the name compactin, was also determined by A. G. Brown, T. C. Smale, T. J. King, J. Chem. Soc. (Perkin I) 1165 (1975). This compound has been found to be a strong inhibitor in vivo of the biosynthesis of cholesterol.

More recently, Monaghan et al. have reported (U.S. Pat. No. 4,231,938) that a methyl analog (Formula I) is formed by the cultivation of a microfungus of the genus Aspergillus and that this product is an even more potent inhibitor of cholesterol biosynthesis.

From the same fermentation, Albers-Schonberg et. al. (U.S. Pat. No. 4,294,846) isolated the dihydro analog of structure IV.

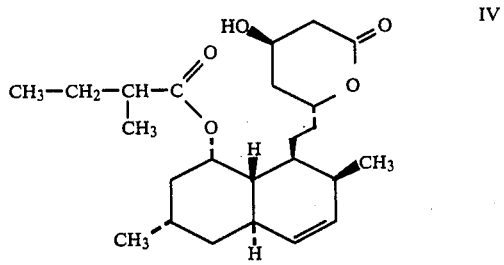

Also more recently, Endo has reported (J. Antibiotics, August 1979, page 1852, and W. German Offenlegungschrift No. 30 06 216), the isolation of a compound identical with Compound I from a cultivation of a strain of *Monascus ruber,* an entirely different microorganisms.

DESCRIPTION OF THE INVENTION

We have found that the hydrogenation of Compounds I and IV over various catalysts produces dihydro (from I) and tetrahydro products, some of which (V, VI and VIII as shown in Flow Sheet A) are potent inhibitors of cholesterol synthesis, while others (e.g. VII) are not.

These new compounds do not appear to be formed in the fermentations described by Endo or Monaghan or Albers-Schonberg. They are stable compounds even in thin films and are potent inhibitors of cholesterol synthesis equal or superior to the compound, ML236B described by Endo in this respect.

The compounds of this invention are highly useful as antihypercholesterolemic agents for the treatment of atherosclerosis, hyperlipemia and like diseases in animals and humans. They may be administered orally or parenterally in the form of a capsule, a tablet, an injectable preparation or the like. It is usually desirable to use the oral route. Doses may be varied, depending on the age, severity, body weight and other conditions of animal or human patients but daily dosage for human adults is within a range of from about 2 mg. to 2000 mg. (preferably 10 to 100 mg.) given in three or four divided doses. Higher doses may be favorably applied as required.

The compounds of this invention also have useful anti-fungal activities. For example, they may be used to control strains of Penicillium sp., *Aspergillus niger,* Cladosporium sp., *Cochliobolus miyabeanus* and *Helminthos-*

*porium cynodnotis.* For those utilities they are admixed with suitable formulating agents, powders, emulsifying agents or solvents such as aqueous ethanol and sprayed or dusted on the items to be protected.

The preparation of the compounds of this invention is described in Flow Sheet A. One starting material is the fermentation product, Compound I, described by Monaghan et al, U.S. Pat. No. 4,231,938. This, depending on the catalyst used, can be hydrogenated to give one of the compounds V or VI or a mixture of compounds VII and VIII. Thus, hydrogenation over tris(triphenylphosphine)chlororhodium in toluene, saturates the 3,4 double bond to give compound VI but hydrogenation over palladium on calcium carbonate, in ethanol not only saturates the 4a, 5 double bond but causes a shift of the 3, 4 double bond to the 4, 4a position (i.e. there is effectively a 1, 4 hydrogenation of the conjugated diene). Hydrogenation over platinum oxide in ethyl acetate completely saturates the polyhydronaphthyl ring to give a mixture of the two isomeric decalin derivatives VII and VIII. The naturally occurring dihydro Compound I, i.e. Compound IV described by Albers-Schonberg et al. (Ser. No. 77,807, filed Sept. 21, 1979) on reduction over palladium on charcoal in ethyl acetate also provides the completely saturated polyhydronaphthalene ring to give only the compound of Structure VIII with the trans ring fusion.

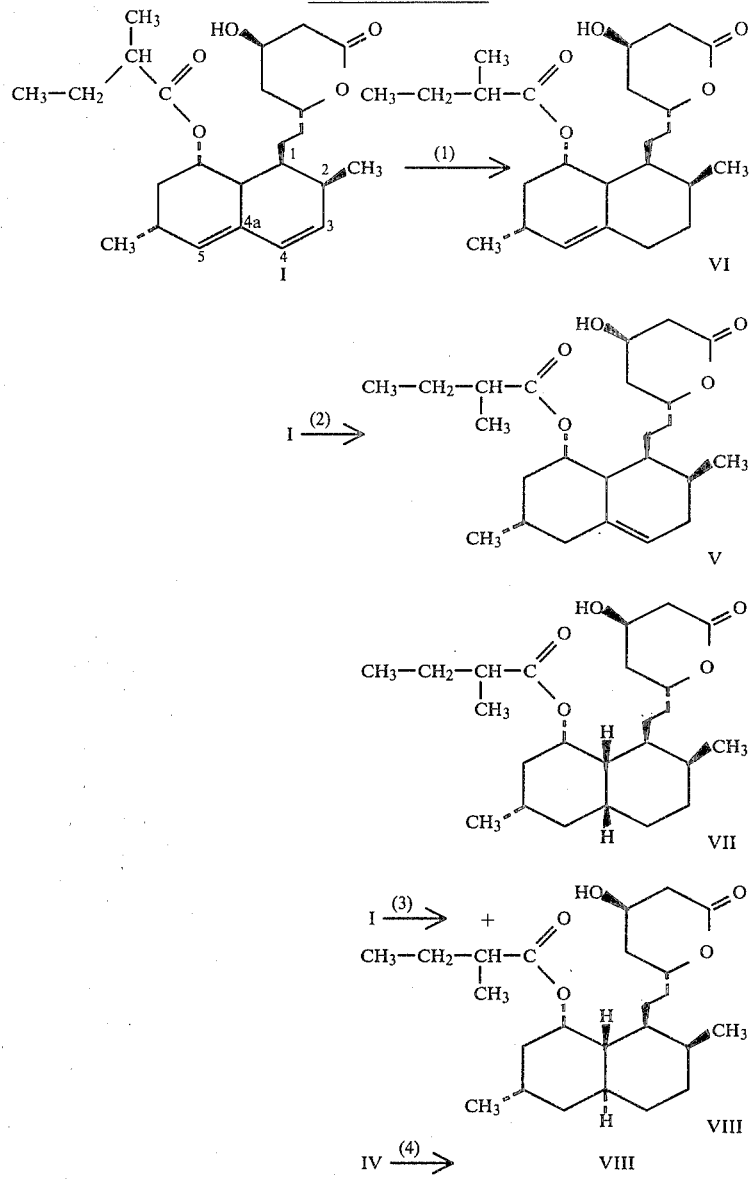

FLOW SHEET A

REACTIONS AND REAGENTS

1. Hydrogenation at about 20°–75° C. and about atmospheric pressure to about 4 atmospheres over tris (triphenylphosphine) chlororhodium in an aromatic solvent such as benzene, toluene or xylene, preferably toluene. Preferred conditions are about 40° C. and about 2–7 atmospheres in toluene.

2. Hydrogenation at about 20°–25° C. and about atmospheric pressure over 5% palladium on calcium carbonate in a lower alkanol such as a $C_{1-3}$ alkanol, especially ethanol.

3. Hydrogenation at about 20°–25° C. and atmospheric pressure over platinum oxide in ethyl acetate.

4. Hydrogenation at 20°–25° C. and atmospheric pressure over 10% Palladium on charcoal in ethyl acetate.

EXAMPLE 1

6α[2-8α-2-S-methylbutyryloxy-2β, 6α-dimethyl-1,2,3,4,6,7,8,8a-octahydronaphyl-1)ethyl]-4β-hydroxy-3,4,5,6-tetraydro-2H-pyran-2-one (VI)

Step A: Preparation of Compound I

1. Fermentation

A tube of lyophilized culture MF-4845 *Aspergillus terreus*, ATCC No. 20542) was opened aseptically and the content suspended in an unbaffled 250 ml Erlenmeyer flask (seed flask) containing approximately 10 ml of the Medium which has the following composition:

| Medium | |
|---|---|
| Corn steep liquor | 5 g |
| Tomato paste | 40 g |
| Oatmeal | 10 g |
| Glucose | 10 g |
| Trace Element Solution | 10 g |
| Distilled water | 1000 ml |
| pH 6.8 with NaOH | |

| Trace Element Solution | |
|---|---|
| $FeSO_4.7H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |
| $(NH_4)_6Mo_7O_{24}.4H_2O$ | 19 mg |
| $ZnSO_4.7H_2O$ | 200 mg |
| Distilled Deionized Water | 1000 ml |

The inoculated flask was incubated for 24 hours at 28° C. on a 220 rpm shaker (2 inch throw). An unbaffled 2 liter Erlenmeyer flask containing 500 ml of the medium was then inoculated with 10 ml of the first stage fermentation growth from the seed mixture. This too was shaken 24 hours at 28° C.

A 200 gallon stainless steel fermentation vat was then charged with 485 liters of a medium comprising:

| Cerelose | 4.5% wt/vol |
|---|---|
| Peptonized Milk | 2.5% wt/vol |
| Autolyzed yeast | 0.25% wt/vol |
| Polyglycol P2000 | 0.25% vol/vol | whose pH was adjusted to 7.0. This was sterilized 15 minutes at 121° C. One liter of the second stage above was then charged and the mixture was incubated at 85 rpm for 12 hours then 130 rpm for 84 hours at 28° C. with an air flow of 5 cfm for 12 hours then 10 cfm for 84 hours.

2. Isolation a. Extraction

Two batches of one hundred gallons of whole broth were combined, acidified with stirring to pH 4.1 by careful addition of 800 ml of concentrated hydrochloric acid, and extracted by addition of 75 gal of ethyl acetate and further stirring for two hours.

About 25 lbs of a silicaceous filter aid was then added and the total slurry was pumped through a 24-inch filter press. An additional 75 gal of ethyl acetate was used to wash the press cake and continue the extraction, by reversing the direction of pumping through the press four times. Then all of the wash solvent was discharged from the press and combined with the first filtrate. The two-phase filtrate was allowed to settle, and the water layer removed. The ethyl acetate layer was washed with 10 gal of deionized water, the phases were allowed to separate and the ethyl acetate extracts were concentrated under vacuum to a residue of about 10 gal.

b. Lactonization

Ethyl acetate extracts from an additional three hundred gal of broth were added to the above extract and the volume was reduced to about thirty gal. by vacuum distillation. About fifty gal. of toluene was added, and the batch was concentrated under vacuum to 32 gal.; this step was repeated; then sufficient new toluene was added to bring the volume to 75 gal. Without vacuum, the batch was brought to reflux and maintained there for two hours, with a temperature over 106° C.

This solution was then concentrated under vacuum to a small volume, which was further concentrated to an oily residue in a large rotary evaporator under vacuum.

c. Chromatography on Silica Gel

The extract obtained above was flushed free of other solvents by addition of 2 gal. of methylene chloride and reconcentration to an oil.

The oily residue was dissolved in about 5 gal. of ethyl acetate-methylene chloride (30/70; v/v) mixture, and a slurry was made by addition of 2.8 kg of silica gel.

The slurry was loaded as a level layer on the top of a 12 in.×50 in. silica gel column packed in the same solvent mixture.

Elution was with ethyl acetate-methylene chloride (40/60; v/v) at 800 ml/min. A forerun of 10 gal, then further fractions of 4 gal. each were collected.

Fractions 6–10 inclusive were concentrated under vacuum to an oily residue which was dissolved in hot ethyl acetate, treated with decolorizing carbon, filtered hot, and cooled. Crystals of Compound I were filtered off and the mother liquors were concentrated to an oil. The crystalline material (I) after recrystallization from ethanol has m.p. 170°–171° C.

Step B: Preparation of 6α[2-(8α-2-S-methylbutyryloxy-2β,6α-dimethyl-1,2,3,4,6,7,8,8a-octahydronaphyl-1)ethyl]-4β-hydroxy-3,4,5,6-tetraydro-2H-pyran-2-one (VI)

A mixture of 50 mg (0.1236 mmol) of Compound I and an equal molar amount (114.35 mg., 0.1236 mmol) of tris-(triphenylphosphine)-chlororhodium in 10 ml of dry toluene was hydrogenated at room temperature for 6 days, with a total uptake of 14.6 ml of hydrogen. The mixture was evaporated in vacuo to dryness. The red filtrate was subjected to preparative thin layer chromatography on silver nitrate impregnated silica plates and was developed twice in 10% ethyl acetate-ether system. The yield of compound VI was 22.3 mg.

Mass spectra (M/e): 406 (m+); 304 (m-102); 286 (m-102-18).

nmr ($CDCl_3$, 300 MHz): δ 4.37 (m,1H); 4.60 (m,1H); 5.34 (d of t, J=2.5 Hz, 1H); 5.41 (m,1H).

EXAMPLE 2

6α[2-(8α-2-S-methylbutyryloxy-2β, 6α-dimethyl-1,2,3,4,6,7,8,8a-octahydronaphyl-1)ethyl]-4β-hydroxy-3,4,5,6-tetrahydro-2H-Pyran-2-one (VI)

A solution of 1.21 g (3 mmol) of Compound I in 80 cc toluene was added to 1.21 g of tris-(triphenylphosphine)-chlororhodium prereduced in 20 cc of toluene and hydrogenated at 40° and 2.7 atmospheres of hydrogen pressure for 24 hours. The reaction mixture was concentrated in vacuo, taken up in 50 cc of ether, treated with decolorizing carbon and filtered through a diatomaceous filter aid to give, after concentration, an oil, wt. 2.3 g. This product was chromatographed by dry column technique on 250 g of silica gel and eluted with 30% acetone-hexane. From this chromatography were obtained single spot fractions ($R_f$0.48) totaling 650 mg. This product was transparent in the uv and gave a mass ion of 406. Anal. Calcd. for $C_{24}H_{38}O_5$: C, 70.90; H, 9.42. Found: C, 71.17; H, 9.41. The $C^{13}$ nmr of this product demonstrated it to be an approximately 9:1 mixture of the desired Compound VI together with the double bond isomer V. Crystallization from acetone-hexane gave, after several crystallizations, Compound VI (needles) of constant melting point, 113°-115°.

EXAMPLE 3

6α[2-(8α-2-(S)-methylbutyryloxy-2β,6α-dimethyl-1,2,3,5,6,7,8,8a-octahydronaphthyl-1)ethyl]-4β-hydroxy-3,4,5,6-tetrahydro-2H-pyran-2-one (V)

A solution of 80.91 mg (0.2 mmol) of Compound I in 10 ml of absolute ethanol, in the presence of an equal weight of 5% Pd on $CaCO_3$ was hydrogenated at 1 atmosphere until an uptake of one mole equivalent of hydrogen was observed. The catalyst was then removed by filtration and the filtrate was evaporated to dryness (81 mg). After a purification by preparative thin layer chromatography to remove a small amount of by-product dihydro compound VI, 72 mg. of the 1,4-reduction product (V) was isolated Mass Spectra (M/e): 406 (m+); 304 (m-102); 286 (304-$H_2O$);

nmr ($CDCl_3$, 300 MHz); δ 4.38 (m, 1H); 4.64 (m, 1H); 5.28 (d of t, J=3.5 Hz, 1H); 5.48 (m, 1H).

EXAMPLE 4

6α-[2-(8α-2(S)-methylbutyryloxy-2α,6β-dimethyl-1,2,3,4,4aα,5,6,7,8,8a-decahydronaphthyl-1)-ethyl]-4β-hydroxy-3,4,5,6-tetrahydro-2H-pyran-2-one (VIII)

A solution of 80.91 mg (0.2 mmol) of Compound I in 10 ml of ethyl acetate was hydrogenated in the presence of an equal weight of platinum oxide at one atmosphere. An exact 2 mole equivalent of hydrogen was consumed within 1 hour. The catalyst was removed by filtration and the filtrate was concentrated to dryness to give an oil. The cis and trans isomers were separated by preparative thin layer chromatography on silica gel plates (10% ethyl acetate-ether system, bands detected by water spray). The trans isomer (VIII) appears as a more polar spot, compared to the cis isomer, and 60 mg was isolated.

Mass spectra (m/e): 408 (m+); 323 (m-85); 306 (m-102).

nmr ($CDCl_3$, 300 MHz): δ 4.36 (broad singlet, 1H); 4.59 (m, 1H); 5.19 (d of t, J=2.5 Hz, 1H).

EXAMPLE 5

6α-[2-(8α-2(S)-methylbutyryloxy-2α,6β-dimethyl-1,2,3,4,4aα,5,6,7,8,8a-decahydronaphthyl-1)ethyl]-4β-hydroxy-3,4,5,6-tetrahydro-2H-pyran-2-one (VIII)

Step A: Isolation of Compound IV

1. Rechromatography on Silica Gel

Mother liquor residues from broth extract work-ups equivalent to an additional 600 gal. of fermentation production as described in Example 1, Step A were combined with the concentrated mother liquors from Example 1, Step A, in methylene chloride solution. One-half of this solution was taken for further silica gel chromatography. A small aliquot showed a total solids content of 325 g. The solution was treated with 40 g of decolorizing carbon, filtered, and the cake rinsed with methylene chloride. The combined filtrate and washings were concentrated under vacuum to an oily residue. This was redissolved in 800 ml of ethyl acetate/methylene chloride (30/70; v/v) and slurried with 225 g of silica gel. The slurry was loaded on top of a 14×36 cm column bed of silica gel packed in the same solvent mixture. Development was with ethyl acetate/methylene chloride (40/60; v/v). A forecut of three liters was set aside; then fractions of 800 ml each were collected.

2. Chromatography on Reverse-phase Packing

Forty ml from fraction 12 of the above chromatography were concentrated to an oil weighing 500 mg and the oil redissolved in 5 ml acetonitrile. This acetonitrile solution was charged to a ⅜″ OD by 6 ft long stainless steel chromatography column packed with preparative reverse-phase liquid chromatography column packing material "Bondapak C18/PorasilB" (Waters Associates, Inc., Milford, Mass. 01757). The column was eluted with a mixture consisting of (v/v) 55% acetonitrile and 45% 0.05 M ammonium phosphate pH3. The elution volume between 1360 ml and 1700 ml was combined on the basis of refractive index detection. The organic solvent was removed in vacuo and the residual aqueous solution extracted with ethyl acetate. In vacuo removal of the ethyl acetate left 120 mg of compound which crystallized from a concentrated acetonitrile solution yielding crystals of Compound IV, m.p. 129°-131° C.

Step B: Preparation of 6α-[2-(8β-2(S)-methylbutyryloxy-2α,6β-dimethyl-1,2,3,4,4aα,5,6,7,8,8a-decahydro-naphthyl-1)-ethyl]-4β-hydroxy-3,4,5,6-tetrahydro-2H-pyran-2-one (VIII)

A solution of 90 mg Compound IV, from Step A, in 5 cc ethyl acetate and 90 mg of 10% Pd/charcoal was hydrogenated at 24° and atmospheric pressure. Hydrogen absorption was immediate and complete. The reaction mixture was filtered through a diatemaceous filter aid, concentrated in vacuo and crystallized from hexane-acetone, m.p. 126°-127°. It was single spot on tlc (acetone-hexane 30:70), $R_f$0.4.

EXAMPLE 6

Salts

To a solution of 40 mg of the product of Example 1 in 2 ml of ethanol is added 1 ml of aqueous NaOH ($10^{-4}$ moles; 1 equivalent). After one hour at room temperature, the mixture is taken to dryness in vacuo to yield the sodium salt of the free acid form of Compound VI.

In like manner the potassium salt is prepared using one equivalent of potassium hydroxide, the calcium salt using CaO, and the ammonium salt using ammonium hydroxide. Other pharmaceutically acceptable salts are likewise prepared using equivalent quantities of the appropriate base.

In like manner, the products of Examples 3, 4 and 5 can be converted into salts.

EXAMPLE 7

Preparation of Free Hydroxy Acids

The sodium salt produced in Example 6, from the product of Example 1 is redissolved in 2 ml of ethanol-water (1:1) and added to 10 ml of 1 N hydrochloric acid from which the liberated hydroxy acid is extracted with ethyl acetate. The latter solvent is washed once with water, dried and removed in vacuo with a bath temperature not exceeding 30°. The hydroxy acid derived slowly reverts to the lactone on standing.

In like manner, the sodium salts of the products of Example 3, 4 and 5 are converted to the free hydroxy acids.

EXAMPLE 8

To a solution of 4 mg of the product of Example 1 in 1 ml of absolute ethanol is added 0.1 ml 0.1 M sodium ethoxide in absolute ethanol. This solution is allowed to stand at room temperature for one hour, is then diluted into water and extracted twice with ethyl acetate, the ethyl acetate, dried over anhydrous sodium sulfate, is removed in vacuo to yield the ethyl ester of the hydroxy acid of compound VI.

In like manner, by the use of equivalent amounts of methanol, propanol, butanol, isobutanol, amylalcohol, isoamylalcohol, 2-dimethylaminoethanol, benzylalcohol, phenethanol, 2-acetamidoethanol and the like, the corresponding esters are obtained.

In like manner, using the Compounds V and VIII prepared in Example 3 and 4 and 5 in the above procedures, the corresponding esters are prepared.

What is claimed is:

1. A compound of the formula:

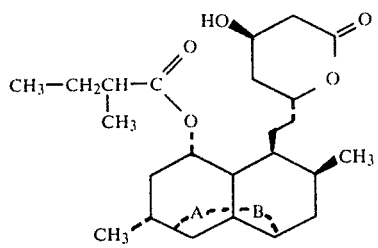

and its free acid form

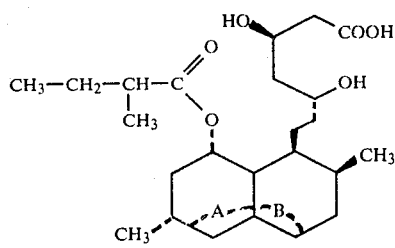

in which the dotted lines indicated as A and B represent optional double bonds, not more than one of A and B being a double bond, and, where neither A nor B is a double bond, the perhydronaphthyl ring is in the 4aα, 8aβ configuration, together with the pharmaceutically acceptable salts of said free acid and the lower alkyl and substituted lower alkyl esters of said free acid in which said substituent is phenyl, dimethylamino or acetylamino.

2. The compound of claim 1 which is the lactone of Formula II.

3. The pharmaceutically acceptable salts of the free acid of Formula III of claim 1.

4. The esters of Compound III of claim 1.

5. The free acid form of Compound III of claim 1.

6. The compounds of claim 2 in which A is a double bond.

7. The compound of claim 2 in which B is a double bond.

8. The compounds of claim 2 in which neither A nor B is a double bond and the ring system is transfused.

9. A method of treating hypercholesterolemia which comprises the administration to a patient in need of such treatment of an effective antihypercholesterolemic amount of a compound of formula II or III of claim 1.

10. An antihypercholesterolemic pharmaceutical composition comprising a pharmaceutical carrier and an antihypocholesterolemic effective amount of a compound of formula II or III of claim 1.

* * * * *